United States Patent [19]

Lew

[11] 3,974,138

[45] Aug. 10, 1976

[54] METHOD OF PREPARING BUTYL POLYGLYCOSIDES

[75] Inventor: Baak W. Lew, Wilmington, Del.

[73] Assignee: ICI United States Inc., Wilmington, Del.

[22] Filed: Sept. 30, 1974

[21] Appl. No.: 510,554

Related U.S. Application Data

[63] Continuation-in-part of Ser. No. 315,542, Dec. 15, 1972, abandoned.

[52] U.S. Cl. .................................................. 536/4
[51] Int. Cl.² ......................................... C07H 15/04
[58] Field of Search ................................ 260/210 R

[56] References Cited
UNITED STATES PATENTS

| | | | |
|---|---|---|---|
| 3,375,243 | 3/1968 | Nevin et al. | 260/210 R |
| 3,450,690 | 6/1969 | Gibbons et al. | 260/210 R |
| 3,565,885 | 2/1971 | Molotsky et al. | 260/210 R |
| 3,721,633 | 3/1973 | Ranauto | 260/210 R |

*Primary Examiner*—Johnnie R. Brown

[57] ABSTRACT

An improved method of preparing butyl polyglycosides wherein the average number of monosaccharide units in the polyglycoside may be controlled is disclosed. The method comprises refluxing, in the presence of an acid catalyst, a mixture of butanol and a monosaccharide wherein the mol ratio of butanol to monosaccharide is equal to from about 1 to about 25 and subsequently distilling off part of the butanol to reduce the mol ratio of butanol to monosaccharide to from 0.6 to 20.

8 Claims, No Drawings

METHOD OF PREPARING BUTYL POLYGLYCOSIDES

BACKGROUND OF THE INVENTION

This application is a continuation in part of application Ser. No. 315,542 filed Dec. 15, 1972; and now abandoned.

FIELD OF THE INVENTION

The present invention relates to a method of preparing butyl polyglycosides. More particularly, the present invention relates to a method of preparing butyl polyglycosides wherein the average number of monosaccharide units in the butyl polyglycoside may be controlled. The process comprises:

a. combining butyl alcohol and a monosaccharide selected from the group consisting of pentoses and hexoses at a molar ratio of butyl alcohol to monosaccharide equal to from 1 to about 25, b. refluxing the resultant mixture in the presence of an acid catalyst, and c. subsequently distilling off part of the butyl alcohol from the reaction mixture to reduce the molar ratio of butyl alcohol to monosaccharide to within the range of from about 0.6 to about 20.

DESCRIPTION OF THE PRIOR ART

Monosaccharides may be represented by the following general formula: $C_n H_{2n} O_n$ and are frequently classified depending upon the number of carbon atoms in the molecule as either trioses (3 carbon atoms), tetroses (4), pentoses (5), hexoses (6), and heptoses (7 carbon atoms).

The monosaccharides are further classified depending upon whether they contain an aldehyde (—CHO) or a ketone ($>c=o$) group in the molecule. Those containing an aldehyde group are referred to as aldoses whereas the ketone group containing materials are referred to as ketoses.

Structurally, the monosaccharides may be represented by either a linear or a cyclic formula.

The following are several examples of monosaccharides which may be used in carrying out the present invention represented by a linear formula.

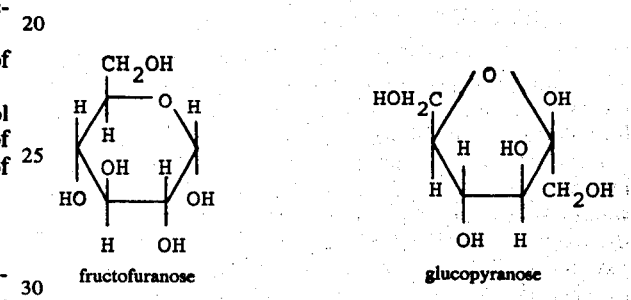

In these structures the carbonyl carbon atom is referred to as the anomeric carbon atom.

In addition to the linear formula discussed above, the monosaccharides may also be represented by a cyclic formula containing a 5 or 6 membered ring. With the cyclic formula the compounds are often referred to as derivatives of pyran or furan, and as such are referred to as pyranoses or furanoses. The cyclic structures are often referred to as hemiacetals in which the carbonyl group of the linear formula has reacted with one of the hydroxyl groups in the molecule. In these formulas, as illustrated below, the anomeric carbon atom now has a hydroxyl group attached to it. This hydroxyl group is referred to as the hemiacetal hydroxyl and is thereby distinguished from the other hydroxyl groups in the molecule which are referred to as the alcoholic hydroxyls.

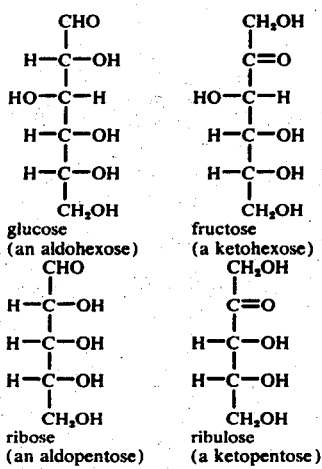

fructofuranose      glucopyranose

Glycosides are prepared by reacting a hydroxyl containing compound, e.g. an alkyl alcohol such as butanol, with one of the aldoses or ketoses referred to above. The reaction takes place between the hemiacetal hydroxyl and the alkyl alcohol (butanol) resulting in a compound wherein the alkyl group is attached to the monosaccharide via an oxygen linkage to the anomeric carbon atom. Compounds having the butyl group in this position are referred to as butyl glycosides.

A variety of alkyl ethers of monosaccharides or polysaccharides wherein one of the alcoholic hydroxyls is reacted with an alcohol are also known in the art. However, the properties of these compounds differ significantly from those of the alkyl glycosides.

Alkyl glucosides have been prepared by reacting an alkyl alcohol with glucose in the presence of an acidic catalyst such as sulfuric acid. See, in this regard, U.S. Pat. No. 3,450,690 issued to Gibbons et al. and U.S. Pat. No. 3,219,656 issued to Boettner. Both of these references relate to the preparation of alkyl monoglucosides; i.e., compounds containing one glucose unit for each alkyl group. These alkyl glucosides are most easily prepared with alcohols having from 1 to 3 carbon atoms in the alkyl group.

Polyglycosides prepared from alcohols containing from 8 to 25 carbon atoms have also been disclosed. See, in this regard, U.S. Pat. No. 3,598,865 issued to Lew.

It is an object of the present invention to prepare butyl polyglycosides in which the degree of glycosidation — i.e. the average number of monosaccharide units per butyl group, may be controlled.

SUMMARY OF THE INVENTION

In accordance with the present invention, butyl polyglycosides having a degree of glycosidation equal to from 1.1 to about 4 are prepared by a process comprising:
a. combining butyl alcohol and a monosaccharide selected from the group consisting of pentoses and hexoses at a molar ratio of butyl alcohol to monosaccharide equal to from 1 to about 25,
b. refluxing the resultant mixture in the presence of an acid catalyst, and
c. subsequently removing butyl alcohol from the reaction mixture to reduce the molar ratio of butyl alcohol to monosaccharide to from about 0.6 to about 20.

DESCRIPTION OF THE INVENTION

As described above, in accordance with the present invention, butyl polyglycosides are prepared by reacting butyl alcohol and a monosaccharide under carefully controlled conditions.

These compounds may be represented by the following theoretical general formula $Bu-O-R-(O-R)_n$ wherein $n$ is an average value equal to from 0.1 to 3.0, Bu is a butyl radical and R is a radical derived from a monosaccharide by formation of a glycosidic bond between the hemiacetal hydroxyl of the monosaccharide and the alcoholic hydroxyl of either butyl alcohol or another monosaccharide. The glycosidic bonds are indicated as —O— in the above formula. As used herein, the term "degree of glycosidation" refers to the average number of monosaccharide units contained in each molecule of the butyl polyglycoside and is equal to from 1.1 to about 4.

The monosaccharides which may be employed in the preparation of the butyl polyglycosides of the present invention include both pentoses and hexoses — i.e., simple sugars containing either 5 or 6 carbon atoms and represented by the following formula:

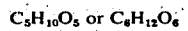

$C_5H_{10}O_5$ or $C_6H_{12}O_6$

The monosaccharides may contain either an aldehyde or a ketone group and may, therefore, be referred to as aldopentoses, aldohexoses, ketopentoses and ketohexoses. Representative monosaccharides which may be employed include, for example, ribose, arabinose, xylose, lyxose, allose, altrose, glucose, mannose, gulose, idose, galactose, talose, ribulose, xylulose, psicose, fructose, sorbose and tagatose. Of these, it is preferred to employ glucose resulting in the preparation of a butyl polyglucoside. Mixtures of these monosaccharides may also be employed.

As an alternative to adding the monosaccharide directly to the reaction mixture, the monosaccharide or mixture of monosaccharides may be formed in situ by including in the reaction mixture a compound such as an oligosaccharide or a polysaccharide which will hydrolyze in the presence of the acid catalyst resulting in one of the monosaccharides mentioned above. Representative compounds hydrolyzable to monosaccharides which may be utilized for this purpose include for example, maltose, lactose, sucrose, raffinose, starch, methyl glucoside and anhydro sugars, such as levoglucosan.

In the preparation of butyl polyglycosides in accordance with the present invention, one of the above mentioned monosaccharides is combined with butyl alcohol. To produce the desired polyglycosides, the molar ratio of butanol to monosaccharide has been found to be critical. Thus, the initial ratio of mols of butyl alcohol to mols of monosaccharide must be in the range of from about 1 to about 25. In preparing butyl polyglycosides, preferred results have been achieved when this ratio is in the range of from about 2 to about 20. Mixtures of monosaccharides may also be utilized as long as the ratio of butanol to total monosaccharide is within the above range.

In carrying out the reaction, an acid catalyst is also included in the reaction mixture. Any acid catalyst known in the art for use in the preparation of acetals may be employed. The preferred acid catalyst is sulfuric acid due to its low cost and ease of removal when the reaction is completed. However, other acid catalysts, such as hydrochloric acid, phosphoric acid, phosphorous acid, toluene sulfonic acid, boron trifluoride, and ion exchange resins in the acid form may also be employed. Although the amount of acid catalyst employed has not been found to be narrowly critical to the preparation of butyl polyglycosides in accordance with the present invention, it is preferred to employ from about .002% to about 2.0% by weight based on the total weight of the reaction mixture. Below about 0.002%, it has been found that reaction times are longer than is desirable and, with more than about 2.0% catalyst, no further increase in reaction rate has been noted. Especially preferred results have been achieved when the amount of acid catalyst is equal to from about 0.005% to about 1.0% by weight based on the total weight of the reaction mixture.

After the components have been thoroughly mixed, heat is applied to the reaction mixture. It has been found that optimum reaction times are achieved by heating the mixture to reflux which is generally in the range of from about 110°C. to about 120°C. If the initial molar ratio of butyl alcohol to monosaccharide is about 5 or higher, the refluxing may be continued until all of the glucose has reacted as evidenced by the production of a clear solution. However, if the initial molar ratio is lower than about 5, it has been found that undesirable by-products are produced if the refluxing is continued for any length of time. Thus, when the initial molar ratio is less than about 5, it is critical that distillation of butyl alcohol be started shortly after refluxing begins. Satisfactory results have been achieved when distillation is begun after about 5 to 10 minutes of refluxing. It has also been found that this change from reflux to distillation must be made no later than at the first evidence of sirupization, which appears as smears on the walls of the reaction vessel. This point is referred to herein as the point of sirupization. It is also possible to prevent the production of undesirable by-products by a partial reflux-partial distillation procedure such as one involving the use of a fractioning column with a reflux ratio control device. However, such a procedure is unnecessarily complicated and expensive and has not been found to be necessary over the much simpler procedure described above.

Although the butyl polyglycosides may be produced by a procedure involving distillation with no prior refluxing, this procedure is not preferred since it results in removal of much of the butyl alcohol before it has had a chance to react with the glucose. Refluxing with an azeotroping agent may also be used. However, this procedure is not preferred since it further complicates the procedure and increases the cost while not resulting in any significant improvement in the product produced.

Thus, in accordance with the improved process of the present invention, when the initial molar ratio of butanol to monosaccharide is equal to less than about 5, the reaction mixture is refluxed for a short period of time and then distilled to remove butanol and reduce the ratio to the desired level as explained in detail below. However, when the initial ratio is greater than about 5, it has been found that refluxing may be continued until all of the monosaccharide has reacted as evidenced by the formation of a clear solution. At this point, the refluxing is terminated and distillation begun to reduce the molar ratio to the desired level. However, here also distillation may be started sooner but this is not critical to the preparation of the desired polyglycoside.

In either case, the distillation is continued until a sufficient amount of butyl alcohol has been removed. As with the initial molar ratio, it has also been found to be critical to the production of butyl polyglycosides in accordance with the present invention that the reduced molar ratio of butyl alcohol to monosaccharide be controlled within a narrow range. Thus, butyl alcohol should be removed until the molar ratio is reduced to within the range of from about 0.6 to about 20. Preferred results have been achieved when the molar ratio is reduced to from about 0.6 to about 18.

The degree to which the molar ratio is reduced has been found to control the number of monosaccharide units in the resulting butyl polyglycoside. Thus, the lower this ratio, the greater the degree of glycosidation in the resulting product. Generally, the degree of glycosidation achieved with the preferred range described above will vary from about 4.0, when the final ratio is reduced to about 0.6, to about 1.1, when the final ratio is reduced to about 18. As used herein, the term "degree of glycosidation" refers to the average number of monosaccharide units per butyl group in the molecule.

As mentioned above, a significant advantage of the process of the present invention is the ability to control the degree of glycosidation of the butyl polyglycodsides which are prepared. This result is achieved by controlling the amount of butyl alcohol remaining in the reaction mixture at the end of the distillation step. The degree of glycosidation of the products from any given reaction can be determined by reference to the following table wherein the final ratio refers to the molar ratio of butanol to monosaccharide at the end of the distillation step.

TABLE

| Final Ratio | Degree of Glycosidation |
| --- | --- |
| 0.6 | 4.0 |
| 0.75 | 3.8 |
| 0.85 | 3.1 |
| 1.1 | 2.4 |
| 1.4 | 2.1 |
| 1.5 | 2.05 |
| 1.7 | 2.0 |
| 1.8 | 1.75 |
| 2.0 | 1.7 |
| 6.0 | 1.3 |
| 9.4 | 1.2 |
| 16 | 1.1 |
| 18 | 1.1 |
| 20 | 1.1 |

TABLE-continued

In addition to removing butanol to reduce the final molar ratio to the desired value, the distillation step also removes, from the reaction mixture, the water formed during the course of the reaction and thereby improves the total yield of butyl polyglycoside. This is due to the fact that the glycoside-forming reaction is reversible and the butylpolyglycoside is hydrolyzed to butyl alcohol and monosaccharide in the presence of acid and water.

After the desired ratio has been reached, the reaction may be terminated by neutralizing the acid catalyst. This may be accomplished by the use of any suitable alkaline material including, for example, sodium hydroxide, potassium hydroxide and sodium carbonate. The resulting butyl polyglycoside may be used without any further treatment as a solution in excess butyl alcohol. If desired, the butyl alcohol may be removed by distillation under reduced pressure.

It has also been found, in accordance with the present invention, that the degree of glycosidation may be further controlled by the addition of butyl alcohol to the reaction mixture after the reduced ratio referred to above has been achieved. Thus, it has been found that, if the reduced molar ratio is equal to 1.2 or higher, additional butyl alcohol may be added and the reaction continued to lower the degree of glycosidation of the butyl polyglycoside. Such a procedure has been found to be the most economical and practical since it requires the least amount of excess butanol and makes most efficient use of the reactor volume.

The number of monosaccharide units in the polyglycosides prepared in accordance with the present invention can be varied over a range of from about 1.1 to about 4. The butyl polyglycosides are useful as humectants, as polyols in the preparation of polyurethanes, and in the preparation of surfactants. They have been found to be particularly useful in the preparation of esters having varying degrees of solubility in water and oils as described in U.S. application Ser. No. 315,541 filed Dec. 15, 1972, and now abandoned by Baak Lew for "Esters of Alkyl Polyglycosides."

In order to describe the present invention so that it may be more clearly understood, the following examples are set forth.

EXAMPLE I

Into a 1-liter flask equipped with a stirrer, thermometer and reflux condenser, there was added 108 grams of glucose (0.6 mol) and 592 grams (8 mols) of n-butyl alcohol. The initial molar ratio of butyl alcohol to glucose was 13.3. To the resulting reaction mixture there was added 0.2 cc. of concentrated sulfuric acid and the mixture was then heated to reflux. After refluxing for 20 minutes, the reaction mixture changed to a clear solution. After an additional 10 minutes, the refluxing was changed to distillation and 185 grams of distillate were removed in a period of 15 minutes thereby reducing the molar ratio to 9.4. The reaction was then returned to total reflux and allowed to reflux for another 15 minutes.

At the end of this time, potassium hydroxide was added to neutralize the sulfuric acid. There resulted a butyl polyglucoside containing an average of 1.2 glucose units per molecule of butyl alcohol; i.e., a degree of glycosidation of 1.2. The excess butyl alcohol may be removed by distillation to recover the solid butyl 1.2 glucoside.

EXAMPLE II

Into a 1-liter flask equipped with a stirrer, a thermometer and reflux condenser, there was added 216 grams (1.2 mols) of glucose and 518 grams (7 mols) of n-butyl alcohol. The initial molar ratio was 5.8. There was then added to the reaction mixture 0.2 cc. of concentrated sulfuric acid; the mixture was heated to reflux and allowed to reflux for 1¼ hours. At the end of this time, the clear solution was distilled to remove 415 grams of distillate in a period of about 30 minutes resulting in a reduced molar ratio of 1.4. The calalyst was then neutralized by the addition of solid sodium hydroxide. The result was a solution of a butyl polyglycoside containing 2.1 glucose units per molecule.

EXAMPLE III

Into a 1-liter flask equipped with a stirrer, thermometer and reflux condenser, there was added 360 grams (2 mols) of glucose and 518 grams (7 mols) of n-butyl alcohol. The initial molar ratio of butyl alcohol to glucose was, thus, 3.5. To this mixture there was added 0.2 cc. of concentrated sulfuric acid and the mixture was allowed to react by refluxing for 35 minutes. At the end of this time, there was a detectable trace of syrupy droplets along the walls of the flask. The total reflux was then changed to total distillation and after 25 minutes of heating the reaction mixture was a clear, colorless solution. After an additional 10 minutes (total distillation time of 35 minutes), 429 grams of distillate had been collected resulting in a reduced molar ratio of 0.85. The reaction was then terminated by the addition of sodium hydroxide. The resulting product was identified as a butyl polyglucoside containing 3.0 glucose units per molecule.

As a comparison, the experiment was repeated except that the reaction mixture was refluxed for 2 hours during which time the amount of syrup increased. At this time heating was discontinued and the reaction mixture allowed to cool. On cooling a large amount of syrup settled out of the reaction mixture and solidified at room temperature. This material was identified as a high molecular weight polysaccharide.

EXAMPLE IV

Into a 3-liter reaction flask equipped with a stirrer, thermometer and reflux condenser, there was added 970 grams (5.4 mols) of glucose and 1,080 grams (14.6 mols) of n-butyl alcohol. Thus, the initial molar ratio of butanol to glucose was 2.7. To the mixture, there was then added 1.2 cc. of concentrated sulfuric acid and the mixture was heated to reflux. After 15 minutes, with much of the glucose still undissolved, the refluxing was changed to distillation. After 45 minutes, of distillation, the reaction mixture was a clear solution and the distillation was continued for an additional 30 minutes until a total of 530 grams of distillate had been removed. Thus, the molar ratio of butanol to glucose had been reduced to 1.6. If the reaction had been terminated at this point, the resulting butyl polyglucoside would have had a degree of glucosidation of about 2.0. However, there was now added 913 grams of n-butyl alcohol thereby adjusting the molar ratio to 3.9. The reaction mixture was refluxed for one hour, at the end of which time the acid was neutralized by the addition of 1.95 grams of sodium hydroxide dissolved in 5cc. of water. The excess butanol was removed by vacuum distillation at 124°C. and 30 mm. mercury resulting in a yield of 1,136 grams of solid n-butyl 1.5 glucoside — i.e., a butyl polyglucoside having a degreee of glucosidation of 1.5.

EXAMPLE V

Into a 1-liter reaction flask equipped with a stirrer, thermometer and reflux condenser, there was added 216 grams (1.2 mols) of glucose, 518 grams (7 mols) of n-butyl alcohol and 0.2 ml. of concentrated sulfuric acid. The initial molar ratio of butanol to glucose was equal to 5.8.

The reaction mixture was refluxed for 1¼ hours, at the end of which time the mixture had changed to a clear solution. The reaction mixture was then distilled until 473 grams of distillate had been collected. The molar ratio was thus reduced to 0.75. The resulting product, after neutralization and isolation as in Example I, was identified as a butyl polyglucoside having a degree of glucosidation of 3.8.

EXAMPLE VI

Into a 1-liter reaction flask equipped with a stirrer, thermometer and reflux condenser, there was added 216 grams (1.2 mols) of glucose, 518 grams (7 mols) of n-butyl alcohol and 0.15 ml. of concentrated sulfuric acid. The initial molar ratio of butanol to glucose was equal to 5.8.

The reaction mixture was refluxed for 2 hours, at the end of which time the clear solution was distilled until 382 grams of distillate had been removed. The molar ratio had thus been reduced to 1.8. The resulting product, after neutralization and isolation as in Example I, was identified as a butyl polyglucoside having a degree of glucosidation of 1.8.

EXAMPLE VII

Into a 1-liter reaction flask equipped with a stirrer, thermometer and reflux condenser, there was added 243 grams (1.35 mols) of glucose, 518 grams (7 mols) of n-butyl alcohol, and 0.2 ml. of concentrated sulfuric acid. The initial molar ratio of butanol to glucose was equal to 5.4.

The reaction mixture was refluxed for 2 hours, at the end of which time the clear solution was distilled until 338 grams of distillate had been removed. The molar ratio had thereby been reduced to 2.0. The resulting product, after neutralization and isolation as in Example I, was identified as a butyl polyglucoside having a degree of glucosidation of 1.7.

EXAMPLE VIII

Into a 1-liter reaction flask equipped with a stirrer, thermometer and reflux condenser, there was added 216 grams (1.2) mols of glucose, 518 grams (7 mols) of n-butyl alcohol, and 0.2 ml. of concentrated sulfuric acid. The initial molar ratio of butanol to glucose was equal to 5.8.

The reaction mixture was refluxed for 1¼ hours, at the end of which time the clear solution was distilled until 420 grams of distillate had been removed. The molar ratio had thereby been reduced to 1.4. The resulting product, after neutralization and isolation as in Example I, was identified as a butyl polyglucoside having a degree of glucosidation of 2.2.

EXAMPLE IX

Into a 1-liter reaction flask equipped with a stirrer, thermometer and reflux condenser, there was added 216 grams (1.2 mols) of glucose, 518 grams (7 mols) of n-butyl alcohol, and 0.2 ml. of concentrated sulfuric acid. The initial molar ratio of butanol to glucose was equal to 5.8.

The reaction mixture was refluxed for 1¼ hours, at the end of which time the clear solution was distilled until 406 grams of distillate had been removed. The molar ratio had thus been reduced to 1.5. The resulting product, after neutralization and isolation as in Example I, was identified as a butyl polyglucoside having a degree of glucosidation of 2.0.

EXAMPLE X

Into a 1-liter reaction flask equipped with a stirrer, thermometer and reflux condenser, there was added 90 grams (0.5 mol) of glucose, 592 grams (8 mols) of n-butyl alcohol, and 0.2 ml. of concentrated sulfuric acid. The initial molar ratio of butanol to glucose was equal to 16.

The reaction mixture was refluxed for 25 minutes, at the end of which time the clear, colorless solution was distilled until 80 grams of distillate had been collected. The molar ratio had thus been reduced to 14.4. There was then added 71 grams of n-butyl alcohol, adjusting the molar ratio to 16. The reaction mixture was refluxed for ½ hour. The resulting product, after neutralization and isolation as in Example I, was identified as a butyl polyglucoside having a degree of glucosidation of 1.1.

EXAMPLE XI

Into a 1-liter reaction flask equipped with a stirrer, thermometer and reflux condenser, there is added 54 grams (0.3 mols) of glucose, 555 grams (7.5 mols) of n-butyl alcohol, and 0.2 ml. of concentrated sulfuric acid. The initial molar ratio of butanol to glucose is 25.0.

The reaction mixture is refluxed until a clear solution results, at which time distillation is begun and continued until 111 grams of butanol have been removed. The molar ratio is thus reduced to 20.0. The reaction mixture is then neutralized resulting in a solution of the butyl polyglucoside.

EXAMPLE XII

Into a 1-liter reaction flask equipped with a stirrer, thermometer and reflux condenser, there is added 180 grams (1.2 mols) of arabinose, 518 grams (7 mols) of n-butyl alcohol, and 0.4 ml. of concentrated hydrochloric acid. The initial molar ratio of butanol to arabinose is equal to 5.8.

The reaction mixture is refluxed until a clear solution results, at which time distillation is begun and continued until 252 grams of butanol have been removed. The molar ratio of butanol to arabinose is thus reduced to 3.0. After neutralization a solution of the butyl polyglycoside results.

What is claimed is:

1. A method of preparing a butyl polyglycoside having a degree of glycosidation equal to from 1.1 to about 4, said method comprising
    a. combining butyl alcohol and a monosaccharide selected from the group consisting of pentoses and hexoses at a molar ratio of butyl alcohol to monosaccharide equal to from 1 to about 25,
    b. refluxing the resulting mixture in the presence of an acid catalyst, and
    c. subsequently distilling butyl alcohol from the reaction mixture to reduce the molar ratio of butyl alcohol to monosaccharide to a final ratio equal to from about 0.6 to about 20, provided that (i) if the initial molar ratio is equal to from 1 to 5, the distillation of butanol is started prior to the point of sirupization.

2. A method, as claimed in claim 1, wherein the monosaccharide is glucose.

3. A method, as claimed in claim 1, wherein the initial molar ratio of butyl alcohol to monosaccharide is equal to from about 5 to about 25.

4. A method, as claimed in claim 3, wherein the reaction mixture is refluxed until a clear solution results.

5. A method, as claimed in claim 1, wherein the initial molar ratio of butyl alcohol to glucose is equal to from about 1 to about 5.

6. A method, as claimed in claim 1, wherein the molar ratio is reduced to a final ratio equal to from about 1.2 to about 20.

7. A method, as claimed in claim 6, comprising
    a. adding additional butyl alcohol to the reaction mixture after the reduced ratio is reached, and
    b. refluxing the reaction mixture.

8. A method, as claimed in claim 1, wherein the reaction is terminated by the addition of an alkaline material to the reaction mixture when the reduced molar ratio is reached.

* * * * *

UNITED STATES PATENT AND TRADEMARK OFFICE
CERTIFICATE OF CORRECTION

PATENT NO. : 3,974,138
DATED : August 10, 1976
INVENTOR(S) : Baak W. Lew

It is certified that error appears in the above-identified patent and that said Letters Patent are hereby corrected as shown below:

Column 2, line 30, " 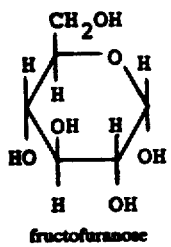 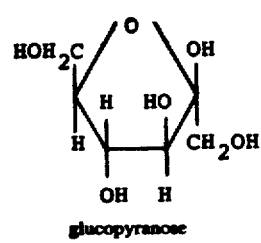 "

should read -- 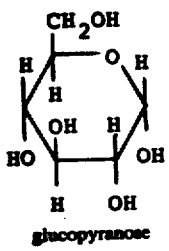 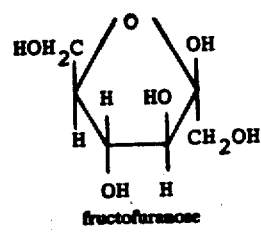 --

Column 7, line 19 "calalyst" should read -- catalyst --

Signed and Sealed this

Twenty-third Day of October 1979

[SEAL]

Attest:

RUTH C. MASON
*Attesting Officer*

LUTRELLE F. PARKER
*Acting Commissioner of Patents and Trademarks*